United States Patent [19]
Klepacki

[11] Patent Number: 5,125,970
[45] Date of Patent: Jun. 30, 1992

[54] MATERIAL AND METHOD FOR COLORIZING DENTAL PROSTHESES

[76] Inventor: John A. Klepacki, 1210 Oakton La., Naperville, Ill. 60540

[21] Appl. No.: 637,381

[22] Filed: Jan. 3, 1991

[51] Int. Cl.⁵ .............................................. C09K 3/00
[52] U.S. Cl. ...................... 106/35; 264/20; 433/203.1
[58] Field of Search ............ 264/20; 433/203.1; 106/35

[56] References Cited

U.S. PATENT DOCUMENTS

| | | | |
|---|---|---|---|
| 2,514,075 | 7/1950 | Kelly | 433/203.1 |
| 3,218,711 | 11/1965 | Connan | 433/203.1 |
| 4,161,410 | 7/1979 | Pellico | 106/35 |
| 4,693,748 | 9/1987 | Kobayashi et al. | 106/35 |
| 4,704,164 | 11/1987 | Amdur et al. | 106/35 |
| 4,744,759 | 5/1988 | Bowes | 433/238.1 |
| 4,828,117 | 5/1989 | Panzera et al. | 206/63.5 |
| 4,970,032 | 11/1990 | Rotsaert | 264/20 |

*Primary Examiner*—William R. Dixon, Jr.
*Assistant Examiner*—Margaret V. Einsmann
*Attorney, Agent, or Firm*—Fitch, Even, Tabin & Flannery

[57] ABSTRACT

A method and agglomerated material for providing special effects in a dental restoration where the agglomerated material is a plurality of powdered particles of colorizing agents bound to form macroscopic shards for direct insertion into a soft, gel-like dental restoration preform to provide the special effects after glazing the preform.

2 Claims, 1 Drawing Sheet

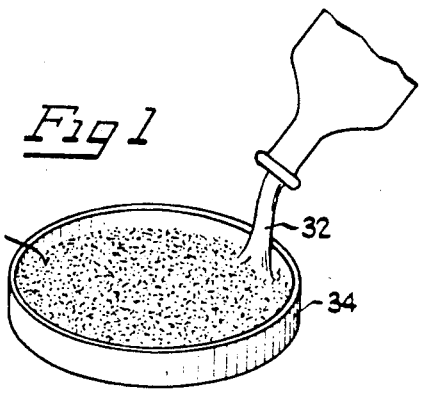
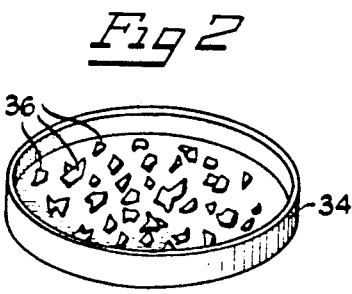
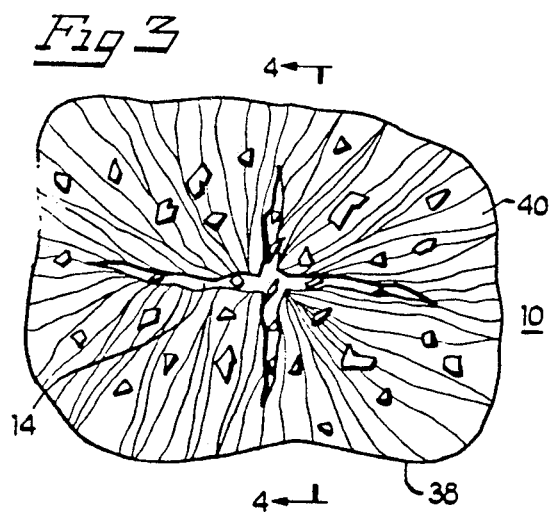
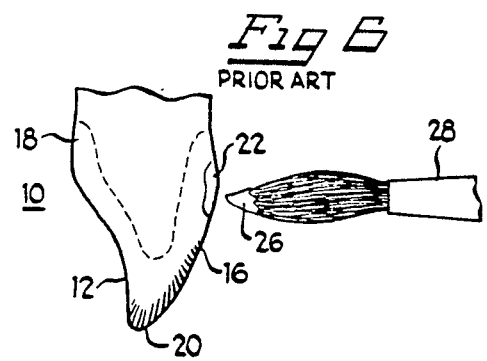
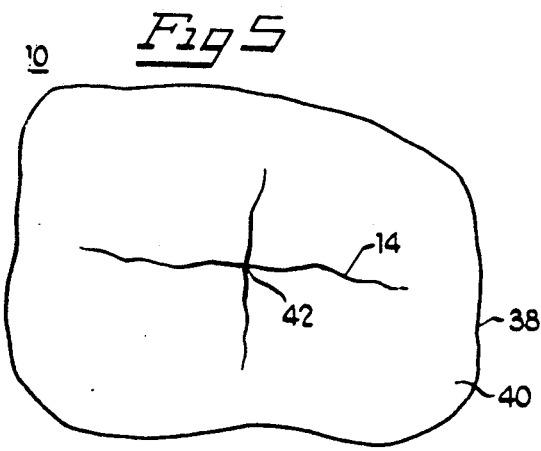
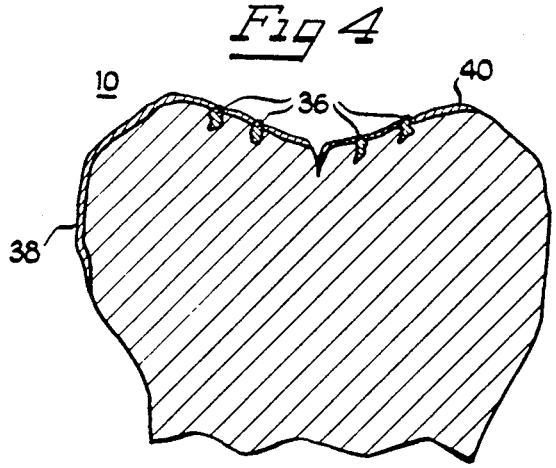

MATERIAL AND METHOD FOR COLORIZING DENTAL PROSTHESES

The present invention relates to materials for colorizing dental protheses and, more particularly, macroscopic materials are provided for direct insertion into preform dental molds to adjust or accommodate color, hue and value to more closely approximate the natural tooth colorization of the individual.

Aesthetics denotes beauty and current dental standards relate aesthetics to natural beauty and thus requires natural appearance, even in a prosthesis placed in an anterior region Shade, anatomy and arrangement of the natural teeth greatly vary among individuals. Aging effects changes in color, translucency and reflectivity in the deep portion of the tooth, as well as the surface luster and characteristics due to attrition on the labial aspect. Other changes may be noted due to age, sex, appearance, and physical attributes of the individual. Although easily sought after, a natural appearance is not easily attainable as the prosthesis may have a china-like appearance, a piano-key like appearance because of a lack of construction, and/or a disharmony of shade from a variation in light source impinging on the device.

Color and translucency interact and interrelate to produce tooth shade, and thus it is important to match the color in hue, chroma and value of the prosthesis with the adjacent teeth. Therefore, reproduction of a natural appearance in the tooth requires not only knowledge of shade construction in the metal-ceramic system but also of the natural teeth. Dentists and technicians often have difficulty in selecting and matching shades in dental prostheses. The precise consideration of coloring of the prostheses may be effected by the technicians perception of color, the light source at the time of manufacture and the objects color, which may be due to reflection, translucence or interference. Although vision is influenced by the effect of consistent chromatic perception, the color of a given object in value and hue between the object and its background seems different due to contrast. Indicative of the difficulty for the technician is the necessity of matching colors on a plaster model where the brightness of the plaster may cause an error. If a crown is fabricated neglecting the shape in the incisal area, total reflection may be completely lost or range over too narrow or wide an area, which may make the tooth appear artificial in color at the incisal area.

Artificial teeth and teeth implants are generally produced from metals, resins and dental porcelain. These materials have their own natural color and texture, which is different than natural teeth and more specifically is different than any individual's tooth color. Various artistic techniques are utilized by the technician to accommodate and match the coloration of a natural tooth to the prosthetic implant to avoid highlighting the existence of the dental implant, which will make the patient more at ease with the prosthesis.

Dental prostheses and more particularly bridges are broadly provided by forming an underlying support post of a metal, such as gold, palladium or platinum. Thereafter, a porcelain overlayment is formed on the support post, shaped to the desired configuration for the individual and fired to provide a hard, shiny tooth. However, the fired tooth porcelain has a distinctive white color that is not generally the color of natural teeth and would not include the natural lines or color changes visible in various parts of natural teeth. The appearance of the prosthesis is affected by numerous factors including the chemical composition of the underlying support post; the composition of the porcelain; the thickness of the tooth cross-section at any point; the morphology of the tooth surface; and, additive coloring agents provided to effect the hue and tone of the tooth surfaces. In addition, the heat treating and firing technique impacts upon the resultant finished porcelain as well as the physical and chemical bonding of the structure, and consequently the appearance of the prosthesis, which is one of the primary considerations of the dentist. Further, any prostheses treatment must provide a structurally sound and stable apparatus for insertion and durability in the patient. Satisfying these goals require the support post to be properly prepared before porcelain fusing, which provides good bond strength and, consequently an increase, of the metal-ceramic system. Indicative of the plurality of steps and operations required to prepare a prosthesis is the meticulous care in providing a solid metal-ceramic bond, as porcelain does not easily or naturally bond to the noble metals, gold, platinum or palladium, which are the base metal of the underlying support posts. However, these same metals are not easily oxidized and generally carry tramp materials, such as tin oxide along at their surfaces. These tramp materials affect the coloration of the overlaying porcelain on the support post and special effects techniques are utilized by the technician to accommodate the color prior to firing and glazing the porcelain preform in a kiln or oven.

Coloration, as noted above, is a critical factor in the preparation and provision of dental implants. Indicative of an effort to control the color of a porcelain is the staining material taught in U.S. Pat. No. 4,693,748-Kobayashi et al., which coloring component is to provide a color closer to the more natural tooth color. These coloring components include additions from among a plurality of metal oxides, which additions add a coloration to the porcelain base to more closely approximate a natural tooth color. Another dental restoration technique provides a plurality of layers including a translucent layer overlaying a more opaque ceramic layer, each layer having a uniform and matching color. This multiple layer structure is taught in U.S. Pat. No. 4,828,117 to Panzera et al., which also discloses a kit for the preparation of the restoration. Further attempts at controlling color have been provided by utilizing an organic liquid binder comprising a mixture of organic liquids with an index of refraction similar to the porcelain powder.

An insert for composite dental restoration is disclosed in U.S. Pat. No. 4,744,759 to Bawer, which provides a composition and technique for micromechanical and chemical bonding with composite resins.

However, none of the above accommodate color correction in the morphology of the restoration. The changes in the special effects may be for dentine effects, incisal effects or surface stains. The dental restorations have been colored with striation-like characteristics by mechanically marking or trenching the preform, providing a colorizing material, such as a colored dentine powder, in the outline with a brush and sealing over the outline prior to firing the porcelain restoration. This requires considerable artistic talent and technique in selecting and applying the coloring agent with a brush, that is the proper amount of the colorant with the correct trench depth.

SUMMARY OF THE INVENTION

The present invention provides thin agglomerated shards of coloring agents in either regular or irregular discrete pods or packages for insertion into dental preforms to provide the desired morphological tooth characteristics and special effects without otherwise sculpting the tooth for these colorizing additions. Further, the colorizing shards are provided in a plurality of colors for selection by the dental technician without concern for the quantity of powder material on a brush end.

BRIEF DESCRIPTION OF THE DRAWING

In the Figures of the drawing, like reference numerals identify like components, and in the drawing:

FIG. 1 illustrates the addition of a binder into a mixing glass with a powder colorizing agent;

FIG. 2 illustrates representative shards of an agglomerated colorizing agent;

FIG. 3 is a plan view of a representative dental restoration;

FIG. 4 is a cross-sectional view of the prosthesis in FIG. 3 taken along the line 4—4;

FIG. 5 is a plan view of a dental preform; and

FIG. 6 is a cross-section of a preform and the insertion of a brushed-on dentine special effect.

DETAILED DESCRIPTION OF THE PREFERRED EMBODIMENT

A dental restoration preform 10 is illustrated in FIGS. 3-6 in plan and cross-section.

Restorations 10 are illustrated in their preform and pre-glazed state for shaping, morphological changes, and special effects in the teeth for their conformation to the desired finished dental restoration. The restoration or prosthesis changes may be along the margins and incisal areas of the teeth, and include indentations 12, grooves 14, coloring 16 and other characteristics of natural teeth. The grooves 14 and morphological characteristics provide areas of reflection and refraction in natural teeth, which add to the color, hue and chroma of the natural tooth in the mouth. Therefore, it is incumbent upon the dental restoration technician to provide not only the white porcelain characteristic for the tooth, but also to provide these reflective and refractive surfaces Consequently, restorations 10 are colored not only in the substrate porcelain but also in the several grooves 14, indentations 12 and other areas.

Referring to FIG. 4, restoration 10 is provided in the dentine 16, the gingival or neck region 18 and in the incisal areas 20 with narrow slits, grooves and color additions in relative relation to the above-noted naturally occurring positions in the teeth. These changes are in addition to the color control of the base porcelain. It is the practice within the art to provide these several prostheses areas with colorations approximating the characteristics of the teeth to be replaced. Accommodation of the colorations must provide for variation of light density, reflection and refraction from the surface and underlying substrate of the porcelain in the teeth. Therefore, coloring additives are selected for addition to the porcelain from among the group of metal oxides including the following: silicon dioxide; aluminum oxide; sodium oxide; potassium oxide; stannic oxide; barium oxide; ferric oxide; boron oxide; magnesium oxide; silica; chromic oxide; cobalt oxide; iron oxide; manganese; nickel oxide; tin oxide; titanium dioxide; vanadium oxide; zinc oxide; zirconium oxide; and indium oxide. These additions are generally available as powder coloring agents and may be colored porcelain powders. The individual colors resultant from the particular oxide are known in the art and will not be specifically discussed here. It is known that combining two or more of these oxides will provide variations on a resultant coloring oxide powder, however the precise blend or color will not be considered here.

Development of tooth structure and preparations of dental restorations require control of both the morphology and color to provide a more natural restoration. The morphology and natural-like appearance of the restoration is enhanced by colorizing from the technician to provide the proper reflective and refractive surfaces, cavities and lines on the tooth surface or subsurface. These lines on the marginal and incisal areas have been provided by applying a coloring agent 24, such as one of the above-noted colorizing agents, to a groove 14 or slot 22 in the preformed restoration.

Colorizing agent 24 is generally a powder applied by a brush tip 26 of brush 28, as shown in FIG. 6, into slot or groove 14 in FIG. 3 and thereafter overlaying porcelain to retain this contrasting addition within the porcelain. Subsequently, the firing or glazing of the porcelain restoration 10 in a kiln or oven provides the glass-like structure for the finished dental insert or restoration 10. Retained colorizing agent 24 provides a contrasting morphological characteristic within the hardened porcelain structure. This morphological characteristic or special effect provides a contrasting point for reflection, or refraction, to more closely approximate the physical characteristics of a natural tooth. Brush application of colorizing agents 24 is hindered by the care required of the technician to provide the proper quantity of a coloring agent at the right depth within the restoration. These requirements provide variations in resultant tooth restoration, which lead to variations for the technician and provide difficulties in reproducing or providing a natural tooth appearance on restorations. Therefore, it is a better technique, if possible, for such applications to minimize the potential hazard for error during restoration formation.

A method has been developed to insert at the proper location with a minimal amount of artistic technique a coloring agent, such as the above-noted metal oxide salts, which are normally provided in a physical powder-like state. As noted, the handling and applying of powders 24 to the tooth restoration crevices requires careful technique and frequently leads to repetitive operations to overcome mishaps during the forming and shaping of the restoration. The present invention provides agglomeration of special effect powders 24 such as by the addition of binders and/or firing in an oven or furnace. Illustrative of this in the powder agglomeration is the addition of a binder 32 in FIG. 1 into a mixing plate 34 with a thin layer of powder 24 to provide an agglomerate. This binder may be an air-drying composition or curable at elevated temperatures by heating. A representative binder, which may be an 11% xylene solvent, 1.6% Kellox oil, 5% plasticizer S-160[Monsanto] and 8-9% AT-51 acrylic binder [Fisher Scientific] and the balance being the metal oxide [ceramic] coloring additive. The binder acts as an agglomerating agent but does not change the physical properties of the powder materials, which binders may contain acrylic polymers or vinyl polymers as well as surfactants, plasticizers, or adhesion, and porosity modifiers. In some cases, the bound powders are fired and thereafter ruptured or broken into discrete glass-like shards and stored in distinct containers. The binder does not chemically interact with the powders to change the color additive property for its inclusion into the porcelain material. The agglomerated or fired mass, which may be provided in any thickness, is broken into a plurality of shards 36, having either irregular or regular shapes as illustrated in FIG. 2.

In an exemplary illustration, upper surface 40 of a molar-like restoration preform 38 in FIG. 5 has crossing grooves 14. Grooves 14 cross at a common point 42 approximately at the center of this tooth, which may be contoured similar to a natural molar. The plurality of grooves 14 and contour lines, as well as the irregular structure of a tooth, are illustrated in FIG. 3 in an exaggerated fashion to demonstrate the field available for the technician for placement of color additives 24 or striations during the manufacture or preparation of a dental restoration. However, upper surface 40 has been provided with a plurality of the coloration shards 36, which do not have to be any one coloring agent, inserted by the technician into a groove 14 or alternatively pressed into the soft preform surface. Each shard 36 may be grasped, such as by a tweezer, and directly inserted into the gelatinous surface of restoration 10 in its preformed state, which shards 36 may be covered over by porcelain or glazing materials. In FIG. 4, insertion of shards 36 into the general center of the tooth structure is illustrated in the cross-sectional view provided along line 4—4 of FIG. 3. In this illustration, shards 36 are generally inserted centrally within the lower reaches of contoured upper surface 40. Shards 36 may also be provided along the surface of the margins of the tooth 10 for overlayment by porcelain prior to firing. Thereafter, the prepared preform may be inserted into a furnace for treatment of the porcelain to provide it with its glass-like surface.

It is appreciated that individual shards 36 of an agglomerated colorizing agent may be inserted in discrete locations along the margins or incisal areas of the tooth preform by tweezers without first furrowing a trench for receipt of the coloring agent. However, it is contemplated that such furrowing may be utilized at the discretion of the technician. In either the unfurrowed or furrowed state, a selected shard 36 may be inserted into the restoration by the technician and it does not require the artistic limitation of a careful brush stroke, material concentration, or furrow depth to attain the correct colorizing effect, as required in the present brush-stroke techniques.

The above-noted shards 36 may be provided in any shape and thickness. In a preferred condition a plurality of shards of colorizing agents, such as the above-noted oxides, would be provided in a pallet or kit-like arrangement for selection by the restoration technician. The kit may include a collection of packaged shards, which packaging may be bottles, blister packs, or pods in a ballet board for example. The precise packaging arrangement is a supplier or user election.

While only specific embodiments of the inventions have been described and shown, it is apparent that various alterations and modifications can be made therein. It is, therefore, the intention in the appended claim to cover all such modifications and alterations as may fall within the scope and spirit of the invention.

What is claimed is:

1. A method for providing colorization effects of hue, chroma and value in a dental restoration, said method comprising the steps of:
    (a) providing a dental restoration preform in a gelatinous state;
    (b) providing particulate colorizing agent from among at least one of silicon dioxide; aluminum oxide; sodium oxide; potassium oxide; stannic oxide; barium oxide; ferric oxide; boron oxide; magnesium oxide; silica; chromic oxide; cobalt oxide; iron oxide; manganese; stannous oxide; nickel oxide; tin oxide; titanium dioxide; vanadium oxide; zinc oxide; zirconium oxide and indium oxide;
    (c) providing a binder agent having a solvent, a plasticizer, and a binder;
    (d) mixing said binder and colorizing agents to form an agglomerate;
    (e) curing and hardening said agglomerate;
    (f) providing at least one macroscopic shard of a colorizing agent from said agglomerate; and
    (g) inserting said shard into said restoration preform to provide said restoration with a desired colorizing effect after glazing.

2. The method of claim 1 further comprising, providing a groove in said preform to receive said inserted shard.

* * * * *